US009035017B2

(12) United States Patent
Berrang

(10) Patent No.: US 9,035,017 B2
(45) Date of Patent: May 19, 2015

(54) METHOD FOR MAKING POLY(HYDRIDOCARBYNE)

(75) Inventor: Peter G. Berrang, Saanichton (CA)

(73) Assignee: Epic Ventures Inc., Saanichton (CA)

(*) Notice: Subject to any disclaimer, the term of this patent is extended or adjusted under 35 U.S.C. 154(b) by 111 days.

(21) Appl. No.: 13/981,585

(22) PCT Filed: Feb. 2, 2011

(86) PCT No.: PCT/CA2011/000134
§ 371 (c)(1),
(2), (4) Date: Jul. 24, 2013

(87) PCT Pub. No.: WO2012/103622
PCT Pub. Date: Aug. 9, 2012

(65) Prior Publication Data
US 2013/0302754 A1    Nov. 14, 2013

(51) Int. Cl.
C08G 61/04 (2006.01)
C08L 65/00 (2006.01)
C09D 165/00 (2006.01)
C25B 11/04 (2006.01)
C08G 61/02 (2006.01)
C25B 3/04 (2006.01)
C25B 3/10 (2006.01)
A61C 1/00 (2006.01)
A61C 13/15 (2006.01)
A61C 19/06 (2006.01)

(52) U.S. Cl.
CPC ............ *C08G 61/02* (2013.01); *C08G 61/04* (2013.01); *C09D 165/00* (2013.01); *C25B 11/04* (2013.01); *C25B 3/04* (2013.01); *C25B 3/10* (2013.01); *A61C 1/0046* (2013.01); *A61C 19/003* (2013.01); *A61C 19/063* (2013.01); *C08L 65/00* (2013.01); *C08G 2261/11* (2013.01); *C08G 2261/332* (2013.01); *C08G 2261/44* (2013.01)

(58) Field of Classification Search
None
See application file for complete search history.

(56) References Cited

U.S. PATENT DOCUMENTS 5,516,884 A    5/1996    Bianconi
6,989,428 B1   1/2006    Bianconi et al.
8,013,109 B2 * 9/2011    Toppare et al. ............... 528/397
2006/0115772 A1  6/2006  Hah et al.
2010/0063248 A1  3/2010  Toppare et al.

FOREIGN PATENT DOCUMENTS

WO    2008/010781 A2    1/2008
WO    WO 2008010781 A2 * 1/2008  ............. C08G 61/02

OTHER PUBLICATIONS

Electrochemical polymerization of hexachloroethane to form poly(hydridocarbyne): a pre-ceramic polymer for diamond production, Nur et al., J Mater Sci (2009) 44: 2774-2779.*
Facile Synthesis of Poly(hydridocarbyne): A Precursor to Diamond and Diamond-like Ceramics, Nur et al., Journal of Macromolecular Science, Part A Pure and Applied Chemistry, (2008), 45, 358-363.*
M. Fryda, TH. Matthee, S. Mulcahy, A. Hampel, L. Schafter, I. Troster, Diamond and Related Materials, 12 (2003) 1950-1956.
Patricia A. Bianconi et al., J. Am. Chem. Soc., 2004, 126(10), 3191-3202.
S. Xu, X. B. Yan, X. L. Wang, S. R. Yang, and Q. J. Xue, J. Mater, Sci. (2010), 45:2619-2624.
D.V. Savchenko, S.G. Ionov and A.I. Sizov, Inorganic Mat. (2010) vol. 46(2):132-138.
A. Zeng, E. Liu, S. N. Tan. S. Zhang, J. Gao, Electroanalysis, 2002, 14, No. 15-16, pp. 1110-1115.
N. W. Khun, E. Liu, J. Nanoscience and Nanotechnology 2010, 10(7), pp. 4767-4772.
S. M. Huang, Z. Sun, C.W. An, Y. F. Lu and M. H. Hong, 2001, J. App. Phy., 90(5), 2601-2605.
Y. Nur, M.W. Pitcher, S. Seyyidoglu and L. Toppare, J. Macromolecular Science, Part A: Pure and Applied Chemistry, 2008, 45(5), pp. 358-363.
Y. Nur, H. M. Cengiz, M. W. Pitcher and L. K. Toppare, J. Material Sci. 2009, 44: 2774-2779.
Katzenmeyer et al., Journal of Nanomaterials, 2009, Article ID 832327.

* cited by examiner

Primary Examiner — James J Seidleck
Assistant Examiner — Peter A Salamon
(74) Attorney, Agent, or Firm — Smiths IP

(57) ABSTRACT

Poly(hydridocarbyne) (PHC) is synthesized by a hybrid, active-metal/electrochemical method by applying a voltage to the electrodes at least one of which is an active-metal, the electrodes being immersed in a trisubstituted halomethane solution. The active-metal electrode and halomethane solution both partake in the electrochemical reaction.

35 Claims, No Drawings

METHOD FOR MAKING POLY(HYDRIDOCARBYNE)

FIELD OF THE INVENTION

The invention relates to a method for making a poly(hydridocarbyne) polymer for use as a ceramic precursor for creating adhesive, thin, cost-effective diamond or diamond-like carbon (DLC) coatings over large, complex surfaces. Said coatings act as a highly corrosion-resistant barrier, and can be doped to be electrically conductive.

BACKGROUND OF THE INVENTION

Diamond and diamond-like carbon (DLC) coatings have great commercial utility for use as protective coatings, especially for electrode coatings, since such coatings can be doped to be electrically conductive, and are highly corrosion resistant even in strong oxidizing solutions in electrochemical applications with high overvoltage (see for example, M. Fryda, Th. Matthee, S. Mulcahy, A. Hampel, L. Schafter, I. Troster, Diamond and Related Materials, 12 (2003) 1950-1956).

Natural diamond is generally comprised of a cubic crystalline form of carbon. DLC, which is a mixture of mostly $sp^3$—hybridized amorphous carbon, has some of the properties of diamond. Historically, DLC has been applied as a protective coating using a chemical vapour deposition (CVD) process, which process is expensive and limited to coating of planar and relatively small, simple surface topographies.

Thus, the discovery by Patricia A. Bianconi, et. al. (J. Am. Chem. Soc., 2004, 126(10), 3191-3202) of the pre-ceramic precursor polymer poly(hydridocarbyne) (PHC) as a source material to form diamond and DLC coatings at atmospheric pressure and relatively low temperature pyrolysis represents a significant new class of material. PHC is a unique polymer which is a structural isomer of polyacetylene, but with a $sp^3$—hybridized, tetrahedrally bound carbon network backbone comprised of $[CH]_n$. Each carbon must contain a hydrogen substituent to prevent conversion to $sp^2$ carbon so as to minimize the ratio of $sp^2$ to $sp^3$ carbon. Bromoform, which has an $sp^3$ tetrahedral structure was used as a starting material.

Thermal decomposition of PHC results in lonsdaleite, a hexagonal form of diamond. Poly(hydridocarbyne) (PHC) is an air-stable solid at room temperature that forms a nanoparticle or colloidal-dispersion in many polar organic solvents. This feature allows for simple, low cost "dip-coatings" of PHC-organic solvent solutions over large, complex surfaces, where said solution can be dried and heated to form adhesive diamond and DLC sub-micron to micron-thick corrosion resistant thin films or conformal coatings.

Thus, there is great interest and utility in synthesizing PHC cost-effectively on a commercial scale.

Additionally, PHC can be used as a precursor material for synthesizing other materials such as, for example, graphite-like nanospheres (see S. Xu, X. B. Yan, X. L. Wang, S. R. Yang and Q. J. Xue, J. Mater. Sci. (2010), 45:2619-2624). The decomposition of PHC can also be used to increase the tensile strength in an exfoliated graphite matrix (see D. V. Savchenko, S. G. Ionov and A. I. Sizov, Inorganic Mat. (2010) vol. 46 (2):132-138.

As carbon, diamond and DLC coatings are highly biocompatible, the application of DLC coatings over implants such as stents, eye and brain electrodes, cochlear devices, pacemakers, defibrillators, and hip, knee, etc. prosthetics is advantageous.

Since such conformal coatings can also be converted to diamond and DLC by light-activation (i.e. UV laser) processes, new applications such as protective DLC coatings over teeth for dental treatment is possible.

DLC coatings can also be made electrically conductive by doping with, for example, nitrogen (i.e. see A. Zeng, E. Liu, S. N. Tan., S. Zhang, J. Gao, Electroanalysis 2002, 14, No. 15-16, pp. 1110-1115), boron (i.e. see M. Fryda, Th. Matthee, S. Mulcahy, A. Hampel, L. Schafer, I. Troster, Diamond and Related Materials 12 (2003) 1950-1956) or aluminum (i.e. see N. W. Khun, E. Liu, J. Nanoscience and Nanotechnology 2010, 10(7), pp 4767-4772).

Alternatively, PHC can be used as a convenient source material for conventional CVD deposition of diamond and DLC coatings by simple heating without addition of hydrogen or an activation procedure. The traditional method of deposition of tetrahedral amorphous carbon contains a portion of $sp^2$ carbon, which tends to contaminate the final CVD deposited diamond or DLC film. However, by controlling the formation of $sp^2$ carbon, such carbon bonding provides for in-situ doping, thereby providing for electrical conductivity.

U.S. Pat. No. 5,516,884 to Bianconi teaches the formation of 3-D tetrahedrally hybridized carbon-based random network polymers where elements such as silicon, germanium, tin, lead and lanthanides can be incorporated into the network backbone. Each carbon atom has one substituent and is linked via three carbon-carbon single bonds into a 3-D network of continuous fused rings. Thermal decomposition of such polymers forms diamond and DLC carbon. Specifically, Bianconi describes the method for making a variety of polycarbynes, including the synthesis of poly(phenylcarbyne-co-hydridocarbyne) in a 99:1 ratio. However, part of the synthesis process involves the use of NaK alloy, an extremely pyrophoric material, under ultrasonic irradiation, in an inert atmosphere, plus various organic solvents, and additional processing and filtration steps, including refluxing with methyl lithium, rendering this low-yield approach highly problematical for commercial production.

Huang et al. (S. M. Huang, Z. Sun, C. W. An, Y. F. Lu and M. H. Hong, 2001, J. App. Phy., 90(5), 2601-2605) use the reductive condensation of a 1,1,1-tricholorotoluene monomer with an emulsion of NaK alloy in tetrahydrofuran under inert atmosphere to synthesize poly(phenylcarbyne). They also provide data on using a pulsed UV laser for converting the poly(phenylcarbyne) to a diamond-like structure.

U.S. Pat. No. 6,989,428 to Bianconi, et al. provides a detailed summary of the prior art for polycarbyne ceramic polymers used to form diamond and diamond-like carbon. Specifically, it discloses details for the synthesis of poly(methyl- and ethyl-silyne) as a precursor of silicon carbide. However, such synthesis again involves a pyrophoric alloy such as NaK, plus a plethora of processing steps involving various organic solvents and long multiple refluxing steps.

Jung-Hwan Hah, et al. in US Patent Application 2006/0115772 A1, in one embodiment, teach the preparation of poly(hydridocarbyne) by the reductive coupling of $CH_n X^3_{4-n}$, where $X^3$ includes a group VII halogen such as fluorine, chlorine, bromine or iodine, and n is an integer from 1 to 3. Since each halomethane requires one substituent hydrogen to prevent conversion to $sp^2$ carbon, the Hah reference to n=2 and n=3 suggests that these versions would not form poly(hydridocarbyne). They describe dissolving the poly(hydridocarbyne) in an organic solvent to create a polymeric film for forming a hard mask for fine pattern photolithographic applications. Their reductive coupling step still requires a metallic compound such as NaK or methyl lithium, and in some embodiments heat, ultrasonic wave, light or combinations thereof. No further details are disclosed. However, their process appears very similar to that described by Bianconi in U.S. Pat. No. 5,516,884.

Recent developments by Yusuf Nur et al. (Yusuf Nur, Michael W. Pitcher, Semih Seyyidoglu and Levent Toppare, J. Macromolecular Science, Part A, 2008, 45(5), pp 358-363) and US Patent Application 2010/0063248 A1, describe a method for making PHC using the electrochemical polymerization of chloroform. Said approach is simpler, and potentially safer, than that given in U.S. Pat. No. 5,516,884 by Bianconi.

The Nur process involves electrolyzing chloroform in the presence of acetonitrile, with tetrabutylammonium tetrafluoroborate as electrolyte, run at −6V under nitrogen for 4 hours at room temperature. Various additional steps (i.e. refluxing with tetrahydrofuran and $LiAlH_4$ for 12 hours), plus final PHC purification steps using dichloromethane and hexane are required. Said process also produces an undefined "insoluble material", and generates chlorine gas, with PHC produced at a 30-40% yield.

In a subsequent publication Nur et al. (Yusuf Nur, Halime M. Cengiz, Michael W. Pitcher and Levent K. Toppare, J. Mater. Sci. 2009, 44: 2774-2779) describe the electrosynthesis of PHC from hexachloroethane. The method used was substantially the same as that using chloroform, with the key difference being that the PHC polymer chain length is bigger using hexachloroethane as a starting material. The methods described by Nur et al. using chloroform and hexachloroethane as starting materials, are still complex, and problematical for producing PHC commercially.

Their method operates the electrochemical cell at −6 V, which exceeds the decomposition voltage of most organic solvents (which tend to decompose at less than 3 volts) thus forming unwanted by-products, including toxic gas such as chlorine gas.

The present invention overcomes the prior art limitations for the synthesis of poly(hydridocarbyne).

SUMMARY OF THE INVENTION

The inventive process for making poly(hydridocarbyne) (PHC) uses at least one active-metal electrode immersed in a trisubstituted halomethane or hexachloroethane solution containing a conductive electrolyte in an electrochemical cell. A relatively small potential is applied between the electrodes of the cell to produce PHC at one or both of the electrodes, in solution or precipitated from solution.

The active-metal forms part of, and partakes, in the reaction within the electrochemical cell to form PHC, the active-metal/halomethane salt and an inorganic halide acid (i.e. HF, HCl, HBr and HI). Depending on the reaction conditions, there may also be the formation of additional parasitic species such as acetylene, polyacetylene, hexahalobenzene, etc. Additionally, the active-metal electrode can react to form a halide salt and other reaction products, which products may coat the electrode surface slowing the reaction process, requiring periodic cleaning of said electrode surface.

Some of the possible precursor trisubstituted halomethanes are: $CHF_3$, $CHClF_2$, $CHBrF_2$, $CHBr_2F$, $CHCl_3$, $CHBrCl_2$, $CHBr_2Cl$, $CHBr_3$, and $CHI_3$. Combinations of said halomethanes can also be used. Four simple, readily available, trisubstituted halomethanes are $CHF_3$ (fluoroform), $CHCl_3$ (chloroform), $CHBr_3$ (bromoform) and $CHI_3$ (iodoform), all of which have an $sp^3$ carbon bond tetrahedral structure.

Hexachloroethane, which also has an $sp^3$ tetrahedral structure comprised of two tetrahedra sharing a common edge, can also be used as a PHC precursor material, but it must first be dissolved in a trisubstituted halomethane solution, or another solvent (such as acetonitrile), as hexachlorethane is a solid at room temperature, sublimes at about 187° C. and does not contain a hydrogen.

Suitable active-metals for the electrode include metals such as lithium, sodium, potassium, magnesium, calcium, zinc, aluminum and silver. It should be noted that certain active-metals such as lithium, sodium, potassium, calcium, magnesium, zinc, powdered aluminum, etc. can react spontaneously and explosively with some trisubstituted halomethanes and hexachloroethane, requiring extreme caution in handling and using these materials.

The active-metal electrode is selected such that is not quite sufficiently reactive to react spontaneously with the halomethane (or hexachloroethane) solution, but rather requires an electrical current to induce such reaction. The voltage applied to the electrodes to initiate the electrochemical reaction is minimized to avoid decomposing the electrolyte, any solvent and halomethane (or hexachloroethane) solution as such decomposition can form various parasitic species. It is advantageous to use the minimum voltage necessary to form PHC. In cases where a solvent (such as acetonitrile) is added to aid in dissolution of any electrolyte species, a voltage less the 3 volts is preferred. Use of higher voltages (e.g. 3-10 volts) will tend to decompose the electrolyte, solvent and halomethane/hexahaloethane, which decomposition can form various parasitic species.

The voltage applied to the electrochemical cell can be DC, where the DC voltage is continuous, pulsed, shaped, with a fixed or variable duty cycle, and where such voltage is less than 10 volts, preferably less than 5.5 volts, preferably less than 3 volts, preferably less than 3 volts. The voltage applied to the electrochemical cell can be AC, where said AC voltage is frequency modulated, chopped or pulse shaped, and where such voltage is less than 10 volts (RMS or peak), preferably less than 5.5 volts (RMS or peak), preferably less than 3 volts (RMS or peak).

If the voltage is DC, only one electrode will partake in the electrochemical reaction to form PHC. If it is AC, both electrodes (assuming they are both active-metals) will partake in the electrochemical reaction to form PHC as the polarity switches back and forth.

By controlling the characteristics of the AC or DC voltage applied to the electrodes during synthesis, the electrochemical reaction for the formation of PHC can be optimized. The use of large surface area electrodes (i.e. maximizing the electrode surface to solution volume) is also preferred, so as to optimize the production of PHC. The use of porous electrodes where the geometric (i.e. footprint) surface area of the electrode is less than the actual surface area is preferred.

In order to provide electrical conductivity to initiate the electrochemical reaction, a seed amount of an appropriate substance may be added to the cell solution. This may comprise a seed amount of the active metal halide salt, an inorganic halide acid or an intrinsically conductive polymer or its salt derivative. A suitable solvent may be required.

By using only a limited number of reactants, and a simple electrochemical process, the inventive process described herein is direct, definable and avoids, or minimizes, parasitic side reactions and toxic gas production. The invention is a relatively low-cost, direct electrochemical method for making poly(hydridocarbyne) using readily available, simple precursor chemicals.

The foregoing was intended merely as a summary and was not intended as an exhaustive narration of the features of the invention, which are more properly appreciated in the context of this entire specification, including the claims.

DETAILED DESCRIPTION OF THE PREFERRED AND OTHER EMBODIMENTS

According to the preferred embodiment, the invention uses a hybrid combination of an active-metal electrode and electrochemical means to form poly(hydridocarbyne) using one or more of a trisubstituted halomethane ($CHX_3$, where X is fluorine, chlorine, bromine or iodine, preferably chlorine or bromine), with an $sp^3$ tetrahedral structure.

The trisubstituted halomethanes $HCF_3$, $HCCl_3$, $HCBr_3$, $ICBr_3$ are one source of $sp^3$ carbon for starting material for the synthesis of PHC polymer via active-metal electrolysis. Other trisubstituted halomethanes that are sources of $sp^3$ carbon are $CHF_3$, $CHClF_2$, $CHBrF_2$, $CHBr_2F$, $CHCl_3$, $CHBrCl_2$, $CHBr_2Cl$, $CHBr_3$, and $CHI_3$.

Alternatively, the trisubstituted halomethane may be replaced by hexachloroethane dissolved in a trisubstituted halomethane solution, such as fluoroform, chloroform, bromoform or iodoform (preferably chloroform or bromoform) or in an organic solvent (preferably acetonitrile).

Since halomethanes are not electrically conductive, electrolyte species such as halide salts, intrinsically conductive polymers or their salt derivatives, and/or inorganic halide acids may be seeded into the solution to provide electrical conductivity to initiate the electrochemical reaction. A solvent, preferably a polar solvent such as acetonitrile, may be added to the trisubstituted halomethane solution to aid in the dissolution of the electrolyte species.

Electrolytes can also generate parasitic compounds, especially if higher voltages are used during electrolysis. Preferably, the electrolyte(s) have a higher over-potential than the halomethane solution or any additional solvent used.

The intrinsically conductive polymer can be such polymers as polyaniline, polyaniline nanofibers, polyparaphenylene, polyacetylene, polyphenylene-vinylene, polypyrrole, polythienylene-vinylene, polytriphenylamine, etc.

If an inorganic halide acid is used as the electrolyte species, it is preferably a non-aqueous inorganic halide acid such as HF, HCl, HBr or HI. Since HF, HC, HBr and HI are gases at room temperature and atmospheric pressure, such gases require dissolution into the electrolysis cell solution, preferably via bubbling.

Alternatively a polyaniline conductive salt (i.e. the emeraldine base) may be added to the halomethane solution to provide electrical conductivity. The addition of N-methyl pyrrolidinone may aid in the dissolution of polyaniline and the emeraldine base.

Equation 1 below represents the basic reaction of the invention. Specific trisubstituted halomethane solutions and reactive-metals will form additional species, not shown in Equation 1 (i.e. dimers such as $Al_2Br_6$). Also, the formation of possible parasitic products, such as acetylene, polyacetylene, hexahalobenzene, etc. are not shown. Additionally, the formation of the halide acid is not shown in the equation.

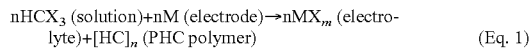

(Eq. 1)

where:
$X_3$ is $F_3$ or $Cl_3$ or $Br_3$ or $I_3$
M is an active-metal such as lithium, sodium, potassium, magnesium, calcium, zinc, aluminum, silver, etc. In one embodiment, the metal M is to comprised of an alloy containing one or more active-metals. $MX_m$ is the metal halide salt formed from fluorine, chlorine, bromine or iodine (i.e. LiF, NaF, $MgF_2$, $CaF_2$, $ZnF_2$, $AlF_3$, AgF; LiCl, NaCl, $MgCl_2$, $CaCl_2$, $ZnCl_2$, $AlCl_3$, AgCl; LiBr, NaBr, $MgBr_2$, $CaBr_2$, $ZnBr_2$, $Al_2Br_6$, AgBr; LiI, NaI, $MgI_2$, $CaI_2$, $ZnI_2$, $AlI_3$, AgI)

a seed amount of an intrinsically conductive polymer, a conductive polymer salt, a halide salt or an inorganic halide acid is added as an electrolyte.

$[HC]_n$ is the PHC polymer with "n" being an integer denoting the chain length the voltage of the electrochemical reaction is minimized to reduce the production of parasitic species the voltage format i.e. AC, DC, pulse length, frequency etc. are optimized to minimize the formation of $sp^2$ carbon, depending at least in part on the reactivity of the active-metal that is selected the rate of reaction is maximized so as to minimize the formation of $sp^2$ carbon the reaction is conducted in an inert atmosphere the temperature of the reaction is run at room temperature, or at a temperature where the trisubstituted halomethane solution is a liquid the trisubstituted halomethane solution is anhydrous and is a liquid at atmospheric pressure In one embodiment, the voltage applied for Equation 1 is DC, where such DC voltage can be continuous, pulsed, shaped, with a fixed or variable duty cycle. In another embodiment, the voltage applied for Equation 1 is AC, where such AC voltage can be frequency modulated, chopped or pulse shaped. Such features are advantageous to optimize the rate of reaction, the PHC polymer chain-length, ring size and particle size. The selection of the specific type of waveform and the voltage that will achieve an optimal yield will depend on the particular active-metal and electrolyte being used. However, the exemplary embodiments detailed below produce acceptable yields.

In the preferred embodiment, both the positive and the negative electrodes are comprised of an active-metal material or alloy thereof. In another embodiment, only one electrode is comprised of an active-metal. In yet another embodiment, the container walls comprise one of the electrodes. It is preferable to create at least one large surface area electrode, and to maximize the surface area of the electrode to the volume of the halomethane solution to create the maximum reactive surface area. Use of porous electrodes, or porous materials coated with reactive-metals is advantageous.

In another embodiment, the active-metal electrode contains at least one non-active-metal dopant material such as carbon, nitrogen, boron or aluminum to provide for electrical conductivity in the resultant diamond or DLC coating made from pyrolized PHC.

In yet another embodiment, the one or more electrically-conducting dopant materials such as carbon, nitrogen, boron or aluminum are added to the halomethane solution during electrolysis to provide for electrical conductivity in the resultant diamond or DLC coating made from pyrolized PHC.

An inert gas, preferably helium, argon or xenon, can be intermittently or continuously bubbled through the electrochemical cell during electrolysis to strip-out or remove any parasitic gases that are generated. However, it should be realized that such stripping process may also remove some of the dissolved inorganic halide acids, which acids can provide beneficial electrical conduction during electrolysis.

The halomethane solution and active-metal must be carefully selected such that the halomethane does not react spontaneously and or explosively either before or during the electrochemical reaction. Active-metals such as lithium, sodium, potassium, magnesium, calcium, zinc or powdered aluminum may also react explosively with many trisubstituted halomethane solutions, thus great care is required in handling reactions involving said materials. Similarly, the choice of active-metals is limited due to the explosive and highly reactive nature of some of these metals with trisubstituted halomethanes.

Various examples of exemplary reactions are shown below. These examples are indicative of various possible combinations, and as such, are not meant to be limiting.

Example 1

Fluoroform ($HCF_3$)

Fluoroform is a gas at room temperature and atmospheric pressure. It has low toxicity and reactivity. $HCF_3$ has been widely used as a refrigerant and fire suppressant.

Although it would be possible to dissolve $HCF_3$ gas in an organic solvent (i.e. acetonitrile), for one embodiment, $HCF_3$ is cooled to below −82° C. (but above −155° C.) to form the liquid phase. Such cooling can be conveniently accomplished by using widely available cryogenic fluids (i.e. liquid nitrogen).

An approach using liquid $HCF_3$ without or with minimal additional solvents, minimizes the introduction of additional compounds which can introduce parasitic chemical reactions during electrolysis.

Since $HCF_3$ has relatively low reactivity, use of an active-metal such as magnesium or zinc as an electrode is possible, though extreme caution is essential when handling and reacting such reactive materials. Accordingly, conductive salts such as $MgF_2$ or $ZnF_2$, intrinsically conductive polymers such as polyaniline, or inorganic halide acids such as HF, can be added to the liquid $HCF_3$ phase to provide for initial electrical conductivity for electrolysis.

Equation 2 shows one embodiment of the electrochemical reaction using Mg as the electrode in a liquid solution of $HCF_3$ with an initial amount of $MgF_2$ salt to act as an electrolyte, in an inert atmosphere, where the AC or DC voltage across the negative and positive electrodes is set low enough to not decompose the liquid $HCF_3$, but still allow the reaction to proceed.

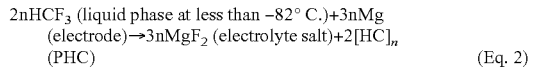
(Eq. 2)

Upon completion, raising the temperature of the electrochemical cell to room temperature will cause the $HCF_3$ to vapourize, and any dissolved PHC and $MgF_2$ to precipitate.

The PHC can then be separated from the $MgF_2$ salt by using solvent extraction methods.

A useful aspect of the reaction shown in Equation 2 is the ability to limit the possible parasitic side-reactions to obtain the highest yield and purity possible for the synthesis of PHC.

For this embodiment, a DC voltage of less than 5.5 volts is sufficient to initiate the reaction.

Example 2

Chloroform ($HCCl_3$)

Although chloroform ($HCCl_3$), which is widely used industrially, is relatively unreactive, it reacts violently with highly active-metals such as lithium, sodium, potassium, magnesium powder or aluminum powder. Accordingly, it is necessary to choose an active-metal (or active-metal shape, i.e. non-powder form) that is not sufficiently reactive with chloroform, but will react, at a low voltage, in an electrochemical cell, without substantially decomposing the electrolyte or any solvent, which decomposition can create unwanted by-products such as acetylene, polyacetylene, hexachlorobenzene, etc.

Accordingly, in one embodiment, at least one magnesium electrode is used in an electrochemical cell with pure (anhydrous) chloroform, in an inert atmosphere, in the dark. Since the electrical conductivity of pure chloroform is very low (i.e. an insulator), it is advantageous to add magnesium chloride salt ($MgCl_2$), an intrinsically conductive polymer, and or HCl acid, as a conductive electrolyte to the chloroform solution. Once the electrochemical reaction is initiated, additional $MgCl_2$ is produced, as shown in Equation 3. The production of parasitic by-products, and production of any HCl is not shown.

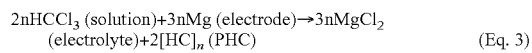
(Eq. 3)

In this example, the initial concentrations of $MgCl_2$ and of HCl are each 0.01% to 3.0% w/w. The reaction is conducted in an inert argon atmosphere at 20° C. in the dark and the voltage applied between the electrodes is 0.5 V DC to 5.5 V DC.

Example 3

Bromoform ($HCBr_3$)

Bromoform ($HCBr_3$) reacts violently with active-metals such as lithium, sodium, potassium, zinc, calcium, powdered aluminum or magnesium. ($HCBr_3$ also reacts violently with acetone and strong caustics). Accordingly, in one embodiment, at least one solid aluminum electrode is used in an electrochemical cell with pure (anhydrous) bromoform.

Since the electrical conductivity of pure bromoform is very low, it is advantageous to add dialuminum hexabromide ($Al_2Br_6$), an intrinsically conductive polymer, and or HBr acid, as a conductive electrolyte to the bromoform solution. Note that $Al_2Br_6$ also reacts violently with water. Once the electrochemical reaction is initiated, additional $Al_2Br_6$ is produced, as shown in Equation 4. The production of parasitic by-products, and production of any HBr is not shown.

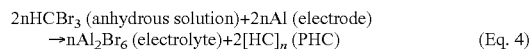
(Eq. 4)

The formation of $[HC]_n$ from Equation 4 will slowly consume the Al electrode, and produce the $Al_2Br_6$ salt, which will precipitate from solution once its solubility in bromoform is exceeded.

One aspect of Equation 4 is that the reaction occurs at a voltage that is sufficiently low to prevent, or only minimally, dissociate $HCBr_3$ to form $sp^2$ bonded species. Thus, the yield of $[HC]_n$ production can be very high, minimizing parasitic side reactions, and allowing for subsequent purification of $[HC]_n$ from the $HCBr_3$ and $Al_2Br_6$ salt using simple, minimal processing steps, such as solvent extraction.

In one embodiment, the thin $Al_2O_3$ passive layer that forms on the surface of aluminum in air is removed in an inert atmosphere, prior to initiating the reaction shown by Equation 4.

For this embodiment, a DC voltage of less than 5.5 volts is sufficient to initiate the reaction.

Example 4

Iodoform ($HCI_3$)

Iodoform is a solid at room temperature that reacts violently with lithium, and is incompatible with reducing agents, magnesium and finely divided silver.

Since iodoform is a solid at room temperature, in one embodiment it can be heated to at least 119° C. in an inert atmosphere, in the dark, to melt the solid to a liquid state. This approach avoids the use of additional solvents and thus the introduction of additional compounds which can introduce parasitic chemical reactions during electrolysis.

Since $HCl_3$ has modest reactivity, use of some active-metals such as silver as electrodes is possible, though extreme caution is essential when handling and reacting such materials. Accordingly, conductive salts such as AgI, or HI acid, can be added to the liquid $HCl_3$ phase to provide for initial electrical conductivity for electrolysis.

Equation 5 shows one embodiment of the electrochemical reaction using Ag as the electrode in a liquid solution of $HCl_3$ with an initial amount of AgI salt (and or HI acid) added to act as an electrolyte, in an inert atmosphere. The electrolysis voltage is set low enough to minimize the decomposition of the electrolyte, but still allow the reaction shown in Equation 5 to proceed. The production of parasitic by-products, and production of any HI acid is not shown.

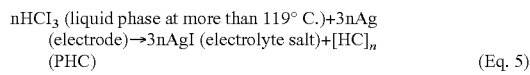
(Eq. 5)

Upon completion, lowering the temperature of the electrochemical cell to room temperature will cause the $HCl_3$ to solidify, whereby the PHC and AgI salt can be pulverized and then separated by solvent extraction.

A key aspect of the reaction shown in Equation 5 is to limit the possible parasitic side-reactions to obtain the highest yield and purity possible for the synthesis of PHC.

For this embodiment, a DC voltage of less than 5.5 volts is sufficient to initiate the reaction.

Example 5

Mixture of Trisubstituted Halomethanes

In one embodiment, one or more mixtures of trisubstituted halomethanes can be used to optimize the formation of PHC during electrolysis. For example, iodoform, which is a solid at room temperature, can be dissolved in bromoform, which is a liquid at room temperature. Such combinations allow for formation of PHC since the halomethanes all have the $sp^3$ carbon bond tetrahedral structure. One or more mixtures of active-metal/halide salts, intrinsically conductive polymers, or inorganic halide acids, can be added to seed the start of the electrochemical reaction.

Example 6

Dissolution of Hexachloroethane in a Trisubstituted Halomethane

Hexachloroethane ($C_2Cl_6$) is a solid at room temperature, that has an $sp^3$ carbon tetrahedral structure where two tetrahedra share a common edge. Such a structure allows this material to form a PHC polymer via active-metal electrolysis. However, $C_2Cl_6$ sublimes at about 187° C. at room temperature, decomposing at about 300° C. Accordingly, in one embodiment, $C_2Cl_6$ is dissolved in a trisubstituted halomethane solution, preferably chloroform or bromoform. Alternatively, a solvent such as acetonitrile, alone or in combination with one or more trisubstituted halomethanes can be used to mix with hexachloroethane.

Since $C_2Cl_6$ also reacts violently with active-metals such as Na, hot Fe, Zn and Al powder, great care must be taken when such a material is dissolved in a trisubstituted halomethane solution, and electrolyzed to form PHC.

Since a solution containing $C_2Cl_6$ and a trisubstituted halomethane, is not electrically conductive, a seed amount of a conductive active-metal/halide salt, such as $Al_2Br_6$, $MgCl_2$, AgI, etc., or an intrinsically conductive polymer, or an inorganic halide acid such as HCl, is added to the solution for electrical conductivity to allow the electrochemical reaction to proceed.

The addition of hexachloroethane to the trisubstituted halomethane solution allows for greater optimization in making PHC, such as forming a larger chain PHC polymer, without introducing parasitic side reactions.

In one embodiment, hexachloroethane is dissolved in chloroform, with at least one active-metal electrode, preferably Ag, and with an active-metal/halide salt, preferably AgCl, and or a halide acid, preferably HCl, added to seed the electrical conductivity. Such a reaction is preferably run at a minimum voltage to minimize parasitic reactions.

In a further embodiment, hexachloroethane is dissolved in bromoform, with at least one active-metal electrode, preferably Ag, and with an active-metal/halide salt, preferably AgBr, an intrinsically conducting polymer, and or a halide acid, preferably HBr, added to seed the electrical conductivity. Such a reaction is preferably run at a voltage of less than 5.5 volts DC.

The invention claimed is:

1. A method for making poly(hydridocarbyne) (PHC) comprising using at least one active-metal electrode immersed in a trisubstituted halomethane solution in an electrochemical cell containing a conductive electrolyte and wherein said active-metal electrode chemically partakes in the reaction with said trisubstituted halomethane solution by reacting with said solution, said active-metal electrode being comprised of one or more elements or alloys thereof selected from among the class of elements consisting of lithium, sodium, potassium, calcium, magnesium, zinc, aluminum and silver.

2. The method of claim 1 wherein said trisubstituted halomethane solution comprises one or more trisubstituted halomethanes selected from among the group consisting of $CHF_3$, $CHClF_2$, $CHBrF_2$, $CHBr_2F$, $CHCl_3$, $CHBrCl_2$, $CHBr_2Cl$, $CHBr_3$, $CHI_3$, and $CHI_3$.

3. The method of claim 1 wherein said conductive electrolyte is comprised of one or more salts, said salts being at least somewhat soluble in said trisubstituted halomethane.

4. The method of claim 3 wherein said salt is a halide salt.

5. The method of claim 4 wherein said halide salt is selected from the group consisting of LiF, NaF, $MgF_2$, $CaF_2$, $ZnF_2$, $AlF_3$, AgF; LiCl, NaCl, $MgCl_2$, $CaCl_2$, $ZnCl_2$, $AlCl_3$, AgCl; LiBr, NaBr, $MgBr_2$, $CaBr_2$, $ZnBr_2$, $Al_2Br_6$, AgBr; LiI, NaI, $MgI_2$, $CaI_2$, $ZnI_2$, $AlI_3$ and AgI.

6. The method of claim 4 wherein said halomethane solution contains an organic solvent to provide for increased solubility of halide salt in said halomethane solution.

7. The method of claim 6 wherein said solvent is acetonitrile.

8. The method of claim 1 wherein said conductive electrolyte is comprised of an inorganic halide acid.

9. The method of claim 8 wherein said inorganic halide acid is selected from among the group consisting of HF, HCl, HBr and HI.

10. The method of claim 8 wherein an organic solvent is added to aid in the dissolution of the halide acid.

11. The method of claim 10 wherein said solvent is acetonitrile.

12. The method of claim 1 wherein said conductive electrolyte is comprised of an intrinsically conducting polymer.

13. The method of claim 12 wherein said intrinsically conducting polymer is selected from among the group consisting of polyaniline, polyaniline nanofibers, polyparaphenylene, polyacetylene, polyphenylene-vinylene, polypyrrole, polythienylene-vinylene and polytriphenylamine.

14. The method of claim 12 wherein an organic solvent is added to aid in the dissolution of said conductive polymer.

15. The method of claim 14 wherein said solvent is acetonitrile.

16. The method of claim 1 wherein said conductive electrolyte is a polyaniline emeraldine base.

17. The method of claim 16 wherein N-methyl pyrrolidinone is added to the halomethane solution to aid with the dissolution of the polyaniline base.

18. The method of claim 1 wherein an inert gas is bubbled intermittently or continuously through the electrochemical cell to minimize parasitic materials formed during electrolysis.

19. The method of claim 18 wherein said gas is selected from the group consisting of helium, argon and xenon.

20. The method of claim 1 wherein a DC voltage is applied between electrodes and said voltage is less than 10 volts.

21. The method of claim 20 wherein a DC voltage is applied between electrodes and said voltage is less than 5.5 volts.

22. The method of claim 21 wherein a DC voltage is applied between electrodes and said voltage is less than 3 volts.

23. A method according to claim 1 where the voltage applied to the electrochemical cell is AC and said voltage is less than 10 volts (RMS or peak).

24. A method according to claim 23 where the voltage applied to the electrochemical cell is AC and said voltage is less than 5.5 volts (RMS or peak).

25. A method according to claim 24 where the voltage applied to the electrochemical cell is AC and said voltage is less than 3 volts (RMS or peak).

26. A method according to claim 1 where said halomethane solution contains a dopant material, wherein said dopant comprises carbon, nitrogen, boron or aluminum to provide for electrical conductivity in the resultant diamond or DLC coating made from pyrolized PHC.

27. A method according to claim 1 said electrode contains a dopant material, wherein said dopant comprises carbon, boron or aluminum to provide for electrical conductivity in the resultant diamond or DLC coating made from pyrolized PHC.

28. A method according to claim 1 where the ratio of the electrode surface is porous such that the geometric surface area is less than the actual surface area.

29. The method of claim 1 wherein one electrode of said cell is a wall of a container of said cell.

30. A method for making poly(hydridocarbyne) (PHC) comprising using an electrochemical cell wherein the positive and negative electrodes of said cell comprise an active-metal and said electrodes are immersed in a trisubstituted halomethane solution containing one or more conductive materials as electrolyte, wherein said active-metal partakes in the reaction with said solution by reacting therewith.

31. The method of claim 30 wherein said conductive materials are selected from among the group consisting of a halide salt, an inorganic halide acid and an intrinsically conducting polymer.

32. The method of claim 30 wherein at least one of said electrodes contains a dopant material, wherein said dopant comprises carbon, boron or aluminum which material becomes incorporated in the PHC to provide for electrical conductivity in the resultant diamond or DLC coating made from pyrolized PHC.

33. The method of claim 30 wherein said halomethane solution contains a dopant material, wherein said dopant comprises carbon, nitrogen, boron or aluminum which material becomes incorporated in the PHC to provide for electrical conductivity in the resultant diamond or DLC coating made from pyrolized PHC.

34. A method for making poly(hydridocarbyne) (PHC) comprising using at least one active-metal electrode immersed in a hexachloroethane solution in an electrochemical cell containing a conductive electrolyte, wherein said active-metal reacts with said solution.

35. A method for making poly(hydridocarbyne) (PHC) comprising using at least one active-metal electrode immersed in a mixture of hexachloroethane and one or more trisubstituted halomethane solutions in an electrochemical cell containing a conductive electrolyte, and wherein said active-metal reacts with said mixture.

* * * * *